(12) United States Patent
Lane (10) Patent No.: US 7,369,645 B2
(45) Date of Patent: May 6, 2008

(54) INFORMATION THEORETIC INVERSE PLANNING TECHNIQUE FOR RADIATION TREATMENT

(76) Inventor: Derek Graham Lane, 307 Guerrero St. #6, San Francisco, CA (US) 94103

( * ) Notice: Subject to any disclaimer, the term of this patent is extended or adjusted under 35 U.S.C. 154(b) by 385 days.

(21) Appl. No.: 11/159,463

(22) Filed: Jun. 23, 2005

(65) Prior Publication Data

US 2007/0003011 A1 Jan. 4, 2007

Related U.S. Application Data

(60) Provisional application No. 60/581,183, filed on Jun. 21, 2004.

(51) Int. Cl.
*A61N 5/10* (2006.01)
(52) U.S. Cl. ....................................... 378/65
(58) Field of Classification Search .. 378/65; A61N 5/10
See application file for complete search history.

(56) References Cited

U.S. PATENT DOCUMENTS

| | | | | |
|---|---|---|---|---|
| 5,647,663 | A * | 7/1997 | Holmes | 600/407 |
| 5,859,891 | A * | 1/1999 | Hibbard | 378/62 |
| 6,038,283 | A | 3/2000 | Carol et al. | |
| 6,411,675 | B1 * | 6/2002 | Llacer | 378/65 |
| 6,560,311 | B1 | 5/2003 | Shepard et al. | |
| 6,735,277 | B2 | 5/2004 | McNutt et al. | |
| 6,741,674 | B2 | 5/2004 | Lee | |
| 6,879,659 | B2 | 4/2005 | Alber | |
| 6,882,702 | B2 * | 4/2005 | Luo | 378/65 |
| 2004/0022438 | A1 * | 2/2004 | Hibbard | 382/199 |

OTHER PUBLICATIONS

Hristov D, Stavrev P, Sham E, Fallone BG. On the implementation of dose-volume objectives in gradient algorithms for inverse treatment planning. Med Phys 2002; 29(5):848-856.
Bortfeld T, Stein J. Clinically relevant intensity modulation optimization using physical criteria. XII ICCR, 1-4, 1997.
Lian J, Cotruz C, Xing L. Therapeutic treatment plan optimization with probability density-based dose prescription. Med. Phys. Apr. 2003; 30 (4); 655-66.
Starkschall G, Pollack A, Stevens CW. Treatment planning using a dose-volume feasibility search algorithm. Int J Radiat Oncol Biol Phys. Apr. 1, 2001;49(5):1419-27.

* cited by examiner

*Primary Examiner*—Edward J. Glick
*Assistant Examiner*—John M Corbett (57) ABSTRACT

A method for fast inverse planning of IMRT treatment plans is disclosed. The method relies on a computationally efficient algorithm for evaluating the gradient of a general class of objective functions, and also on the efficient optimization that is realized due to the directional conjugacy of the objective functions. Several types of clinically relevant objective functions that belong to this class are described. The computational evaluation relies on operations that are commonly used for signal- and image-processing, and so can benefit from a number of well-known acceleration techniques.

15 Claims, 7 Drawing Sheets

INFORMATION THEORETIC INVERSE PLANNING TECHNIQUE FOR RADIATION TREATMENT

CROSS-REFERENCE TO RELATED APPLICATION

This application is entitled to the benefit of Provisional Patent Application Ser. No. 60/581,183 filed 21 Jun. 2004.

FEDERALLY SPONSORED RESEARCH

Not Applicable.

SEQUENCE LISTING OR PROGRAM

Not Applicable.

BACKGROUND

1. Field of Invention

This invention relates to the planning and delivery of radiation for the clinical treatment of disease.

2. Description of Prior Art

Radiation treatment is an established technique that is one of the major treatment modalities for cancer, along with surgery and chemotherapy. Conventional techniques for external beam radiation therapy have required a human planner to first define the parameters of the radiation beams, such as position, direction, and shape. Then the radiation delivered by the resulting beam configuration is simulated, and the resulting radiation dose is evaluated for clinical acceptability. If not acceptable, the beam parameters are modified and the process iterates. This process is referred to as forward planning.

Figure 7:
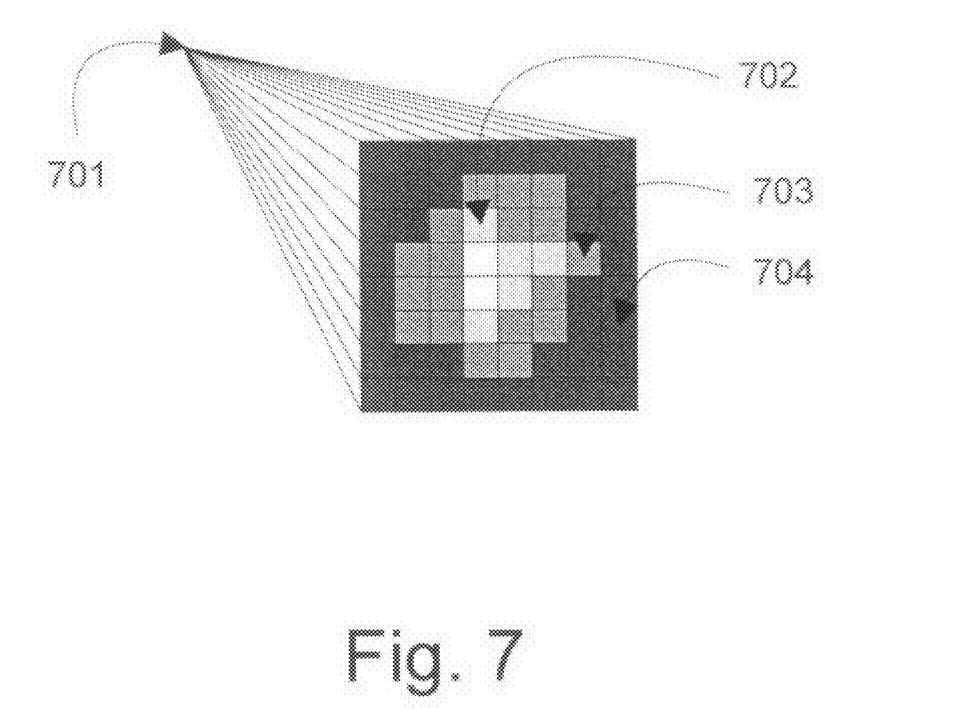
FIG. 7 is a diagram showing the relationship between a single treatment beam and the beamlets comprising that beam. Different beamlets are depicted with differing intensities using grayscale.

Intensity Modulate Radiation Treatment (IMRT) is a more advanced technique that has been developed as a means of achieving better coverage over the tumor (target) and better sparing of nearby critical organs (organs-at-risk). The beams that are delivered in IMRT treatments are defined in terms of a 2-dimensional modulated intensity map across the beam profile. Each pixel in the intensity map is associated with a distinct beamlet, which is the part of the beam's fluence that is passing through that pixel. Each beamlet has an intensity value proportional to the amount of fluence passing through that pixel. FIG. 7 graphically depicts a single beam with sixty-four beamlets having various modulated intensity values. The intensity values are represented in the figure by grayscale shading within the intensity map pixels.

A human planner can in some simple cases directly define the intensity map, in a process similar to forward planning. However, it is generally recognized that an automated algorithm for determining an optimal intensity map, given a set of clinical constraints (such as radiation dose prescription information), is the most robust approach to IMRT planning. This is referred to as inverse planning.

Figure 1:
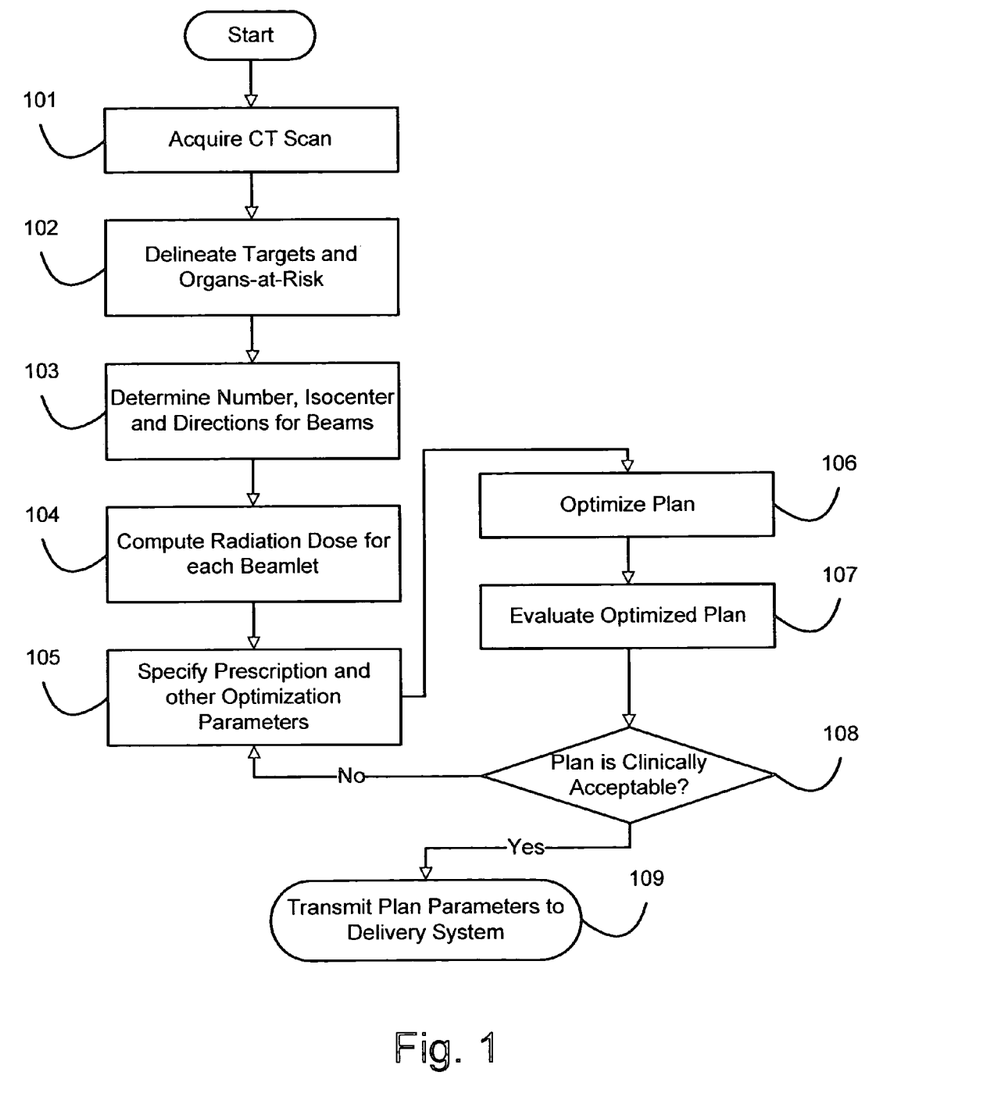
FIG. 1 is a flowchart depicting the basic steps in the IMRT inverse planning workflow.

The workflow for inverse planning of an IMRT plan is given in FIG. 1. This follows the process from acquiring planning CT scans 101 and defining target volumes and organs-at-risk using the planning scans 102. Then the parameters for all treatment beams are determined by the user 103. The dose that would be delivered by all beamlets comprising the beams is simulated 104 using radiation dose computation algorithms that are well known in the art.

Then the prescription and other parameters for the optimization objective function are specified by the user 105, and these are used in the actual optimization algorithm 106 to generate the optimal plan. The resulting plan is evaluated by the user 107. If the resulting plan is not acceptable, the optimization parameters are modified and the process repeats 108. Once the resulting plan is acceptable, the plan parameters are sent to the radiation delivery system 109 for delivery to the patient.

As can be seen, the human planner must still generally iterate with the inverse planning algorithm, as there is no guarantee that the algorithm will generate a clinically acceptable plan. However, the iterations are hoped to be both less complex and fewer in number than that which would be expected for a forward planning scenario. It is highly desirable for the inverse planning algorithm to be as fast and accurate as possible, as this allows the human planner to quickly modify parameters and then evaluate the resulting optimized plan.

Inverse Planning and Optimization

An IMRT inverse planning algorithm essentially works by determining the optimal set of beam parameters satisfying a figure of merit for the plan. If the figure of merit can be expressed as a computable function possessing certain properties, the inverse planning problem can be formulated as a general optimization problem with the figure-of-merit function serving as the optimization's objective function.

In the case of IMRT plans, each beam has a unique intensity map that varies across the two dimensional plane parallel to the beam's central axis. The intensity map is typically represented as a set of sample values on a two-dimensional grid. Each pixel on this intensity map grid then corresponds to the intensity of an individual beamlet. The total beam is comprised of all of the weighted beamlets. FIG. 7 graphically depicts the relationship between beamlets and a treatment beam. All beamlets within the beam originate from a common source point 701. Each beamlet has an intensity value, with some being delivered with a high intensity 702, some with a moderate intensity 703, and some with a low intensity 704.

The dimensionality of such an objective function can be very large. Depending on the resolution of the beamlet representation, it can be hundreds or thousands of dimensions for a clinically realistic plan.

Optimization and the Objective Function

The generalized optimization problem involves determining the input parameters for a specified scalar-valued objective function such that the function assumes a globally minimum (maximum) value. A number of robust algorithms have been developed that can be applied to the general optimization problem [Press et. al. (1993)]. Each of these algorithms has strengths and weaknesses, and the effectiveness of a particular algorithm depends, at least partially, on the properties of the objective function.

The objective function acts as a map for the optimization algorithm, guiding it either to a global optimum or, if acceptable, a local optimum which is suitably close to the global. The number of iterations needed to find the optimum, and the quality of the optimum if sub-global, again often depends on properties of the objective function.

One property of the objective function that can play a significant role in the performance of the optimization algorithm is the ability to efficiently evaluate the mathematical gradient of the objective function. The gradient of a function at a point is the direction of steepest ascent at that point. Knowing the gradient for a high-dimensional objective function can significantly reduce the time needed to search for an optimum, because it specifies the direction along which an optimum may be found. Without gradient information, the optimization may spend an inordinate amount of time searching in "useless" directions.

A second important property of the objective function is referred to as directional conjugacy. This is also a significant issue for problems with large input parameter dimensionality. Directional conjugacy becomes an issue when the objective function has a large number of long, narrow valleys that are not orthogonal to the parameter coordinate axes, or to each other. As the optimization proceeds, each of the iterations is typically carried out along a particular direction. If the objective function is not directionally conjugate, the optimization along a particular direction may "spoil" previous optimizations along other directions. Thus the optimization algorithm has to re-optimize along the previous directions, resulting in wasted iterations.

Clearly an advantageous objective function for inverse planning would possess both of these properties: an efficiently computable gradient, and good directional conjugacy. Of course, the objective function also would need to do a good job as a figure of merit for treatment plans—i.e. clinically more desirable treatment plans would need to be scored better by the objective function than less desirable ones.

Linear Programming Approaches

The linear programming approaches are based on the observation that the sum of weighted beamlets to form total dose can be formulated as a (possibly large) matrix problem. In this case, the matrix relates beamlets to particular voxels, so the matrix is a linear transformation from beamlet weight state vector to dose matrix state vector.

Then, if a target dose matrix can be formed, the corresponding beamlet weights can be computed by multiplying by the inverse of the matrix. In the general case where the matrix is not square, this becomes a matrix pseudoinverse problem. Such a problem is a type of least squares optimization with a purely quadratic objective function. A quadratic objective function is ideal with respect to the aforementioned criteria: efficiently computable gradient and directional conjugacy.

However, this approach immediately leads to problems with respect to the clinical acceptability (and physical plausibility) of the solution, because the resulting beamlet weight vector is likely to contain physically unrealizable negative weights.

U.S. Pat. No. 6,882,702 to Luo (2005) proposes a solution for this issue. The disclosed invention uses iterations that gradually remove negative weights from the problem. This is based on a modified objective function that includes a term to penalize negative beamlet weights. The iterations continue until the contribution to the total radiation dose due to negative beamlet weights is minimize. This alteration in the objective function still allows efficient gradient calculation, but compromises directional conjugacy.

Furthermore, one of the requirements of this approach is that an initial "ideal" radiation dose distribution in 3-dimensions be synthesized as an input to the objective function. In many clinical situations, specifying the relevant statistical characteristics of the desired dose distribution, such as min/max dose to volumes-of-interest (VOIs), is preferable to physically spelling out the intended target distribution in 3-dimensions.

Quadratic Objective Functions

One of earliest methods of specifying the statistical characteristics of the desired dose distribution is using quadratic dose-based objective functions [Bortfeld et. al. (1997)]. The gradient for these objective functions are easy to compute, and they possess good directional conjugacy as the quadratic terms are often nearly orthogonal to each other. The resulting optimizations can be implemented readily using a standard gradient-based algorithm, such as the steepest descent or conjugate gradient algorithms.

However, the clinical acceptability of the simple quadratic objective functions is an issue. For the target regions, the quadratic objective function can express the desirability of a minimum target dose, with high dose homogeneity. For organs-at-risk, however, it is more difficult to effectively capture the clinically desirable dose distribution. This is because organs-at-risk can often be partially irradiated without significant side effects. Thus it is often advantageous to allow partial volume irradiation of organs-at-risk in order to increase target coverage. Specifying that partial volume irradiation is allowable for organs-at-risk is difficult using quadratic dose-based objective functions.

U.S. Pat. No. 6,560,311 to Shepard et. al. (2003) uses a quadratic dose-based objective function as the first preferred embodiments. In the described optimization process, at each iteration the parameter values (e.g. beamlet weights) are changed and the objective function is re-evaluated. The new parameter values are kept only if the new objective function value is better than the previous parameter values. This optimization approach is intrinsically less efficient than utilizing gradient information to first choose the direction of optimization.

U.S. Pat. No. 6,735,277 to McNutt et. al. (2004) also specifies a preferred embodiment with a quadratic objective function. The preferred optimization is a quasi-Newton gradient-based optimization. The disclosed invention is a method of dividing the beamlet weights into independent groups, and optimization each group in succession. This is equivalent to partitioning the original high-dimensional objective function in to a set of independent lower-dimensional objective functions. Then, after finding the optimum of all of the lower-dimensional objective functions, these subordinate solutions are recombined into a single solution. This solution is hoped to approximate an optimum for the original problem. The sufficiency of this approximation depends upon the extent of interdependencies among the beamlet weight parameters, which may be extensive for complex target geometries.

Partial Volume Constraints

In order to represent the partial volume effects for organs-at-risk, the quadratic objective functions have been extended by various authors to include partial volume constraints [Starckschall et. al. (2001)]. Whereas a typical quadratic term might express the constraint "deliver at least 80 Gy to the target region", a partial volume constraint might express "deliver no more than 40 Gy to no more than 25% of the organ-at-risk". By combining multiple terms of this form, it becomes possible to describe the expected shape of the distribution of radiation dose to the target or organ-at-risk. This distribution is typically depicted for clinical purposes as the dose-volume histogram (DVH). In its differential, relative form, the dose-volume histogram is the curve that shows the percent volume of the region of interest that receives a certain amount of radiation dose.

Starckschall et. al. (2001) combined the concept of partial volume constraints with a gradient-based optimization algorithm. In order to evaluate the gradient, however, they numerically evaluate the partial derivatives of the objective function. This is a computationally costly approach that involves evaluating the objective function for a given set of parameters, and then changing each parameter one-by-one by a small amount and re-evaluating the objective function. By doing this for all dimensions, it is possible to evaluate the gradient for the entire parameter space. However, for a beamlet weight-based objective function the amount of time needed to numerically evaluate the gradient can be quite large.

Also, the proliferation of terms in the objective function as more partial volume points are added results in an increasingly complex objective function. However, limiting the partial volume points to a small number can degrade the directional conjugacy of the objective function, as the partial volume constraints correspond to components of the objective function that are often not orthogonal to each other.

U.S. Pat. No. 6,560,311 to Shepard et. al. (2003) also specifies an alternative embodiment using an objective function with partial volume constraints, based on formulae disclosed by Bortfeld et. al. 1997. There is no disclosure of an efficient method of evaluating the gradient of the enhanced objective function, and the iterative optimization algorithm does not make use of gradient information.

U.S. Pat. No. 6,038,283 to Carol et. al. (2000) uses a objective function based on the cumulative dose-volume histogram (CDVH). The method of formulating the CDVH, by division into piecewise-linear regions and then assigning weights for each region, appears to be equivalent to the partial volume constraint approach. The optimization method disclosed, simulated annealing, is a stochastic iterative optimization algorithm that provides no opportunity to take advantage of explicitly computed gradient information.

Direct Gradient Evaluation with Partial Volume Constraints

Hristov et. al. (2002) builds on the Starckschall method and demonstrates that, in theory, it is possible to directly evaluate the gradient of an objective function that incorporates partial volume constraints. To do this, they build up an analytical expression for the objective function using the Heaviside function (unit step function). The use of the Heaviside function follows from their expression of the partial volume constraints in terms of the cumulative dose-volume histogram (CDVH). This follows the practice of Starkschall and others, and is consistent with the clinical practice of using the cumulative forms of the DVH for evaluating plans.

There is a significant theoretical issue with using Heaviside functions in the construction of an objective function. The derivative of the Heaviside function is the Dirac mass, which is a generalized function that assumes a value of zero everywhere except at the origin (where its value is undefined). Because the objective function is intended to act as a map to guide the optimization algorithm, it is desirable for its gradient to yield useful information about the direction that the optimization should proceed. However, in the pure theoretical case, a gradient built up from Dirac masses is unable to point in any direction at all (as it is always zero everywhere except at a finite number of infinitesimal points, where it is undefined).

To address this problem Hristov et. al. uses a discrete approximation to the Dirac mass, the discrete impulse function. This provides some guidance to the optimizer, but it results in an objective function that is piece-wise linear. Such an objective function can be highly fragmented and suffers from serious directional conjugacy problems. This would only be exacerbated by the addition of more partial volume points.

PDF-Based Optimization

Lian et. al. (2003) pursues a conceptually distinct approach by proposing that the target DVH for a particular structure could be well-represented using probability density functions (PDFs). They recognize the value of formulating the objective function using the differential form of the DVH over the cumulative form. The advantage is that the differential DVH (when normalized) is essentially a PDF for dose distribution. This is more consistent with a statistical analysis approach, and provides benefits in the formulation of the objective function over the Heaviside-based objective function that Hristov et. al. employed.

Their approach begins with unimodal gaussian distributions as the target differential DVH (PDF), so that the corresponding target cumulative DVH was the error function shifted to the expected dose for the structure. This has advantages for both target and organ-at-risk, as in reality both types of structures never achieve perfect Heaviside-like distributions. By varying the sigma of the gaussian PDF, different effective slopes can be modeled, which is useful for representing the partial volume effects of an organ-at-risk provided that the set of corresponding partial-volume constraint points lie roughly on a sigmoidal curve.

Additionally, they explore more sophisticated target PDFs, with puzzling results. This included the peculiar asymmetrical under-dosing problem, which could have been due to problems in the method by which they were sampling their prior distribution. It is difficult to ascertain the underlying cause of this problem, as there is an absence of information disclosed about the exact form of the optimization employed.

It is not clear whether any attempt is made to explicitly incorporate gradient information, and no description is given as to how the gradient could be calculated given the PDF formulation. It appears that the approach utilizes a stochastic, Monte-Carlo-like optimization that randomly samples from the possible plan states and then computes the corresponding objective function value. This would probably suffer considerably from scalability problems (moving from 2D to 3D, for instance).

BRIEF SUMMARY OF THE INVENTION

The present invention describes a fast method for inverse planning that allows for easier interaction and more robust solutions.

The present invention derives an analytical expression for the gradient of a DVH-based objective function, with the benefits of the statistical analysis approach intrinsic in Lian's PDF-based objective function. This results in a fully generalized DVH-matching objective function, where any arbitrary, continuous, positive definite function can be used as the target DVH. The resulting objective function possesses both properties of interest: effectively computable gradient and good directional conjugacy. Thus the present invention benefits both from the efficiency of a gradient-based optimization and the clinical utility of an objective function that is able to effectively represent partial volume constraints.

Furthermore, it can be readily extended to more sophisticated, non-linear objective functions that incorporate complex biological effects. These include the tumor control probability (TCP) and normal tissue complication probability (NTCP) statistics [Mohan et. al. (1994)].

The computational form of the objective function (and the more sophisticated versions) can benefit from established methods in accelerated digital signal processing, so the computational efficiency of the resulting inverse planning algorithm should compare quite favorably to existing systems. This can also benefit from the use of graphics and image processing hardware acceleration that is now commonly available on off-the-shelf desktop computers. The increased efficiency can also be used to expand the parameter space that is being searched, for instance to include beam angles in the parameters.

The preferred embodiment of the invention is a computational device adapted to allow specification of the objective function and calculation of the optimum treatment parameters, coupled with a radiation delivery device capable of delivering the radiation based on the computed optimal plan.

DETAILED DESCRIPTION

Theory of Operation-Functional Histogram for an Image or Volume

Figure 4:
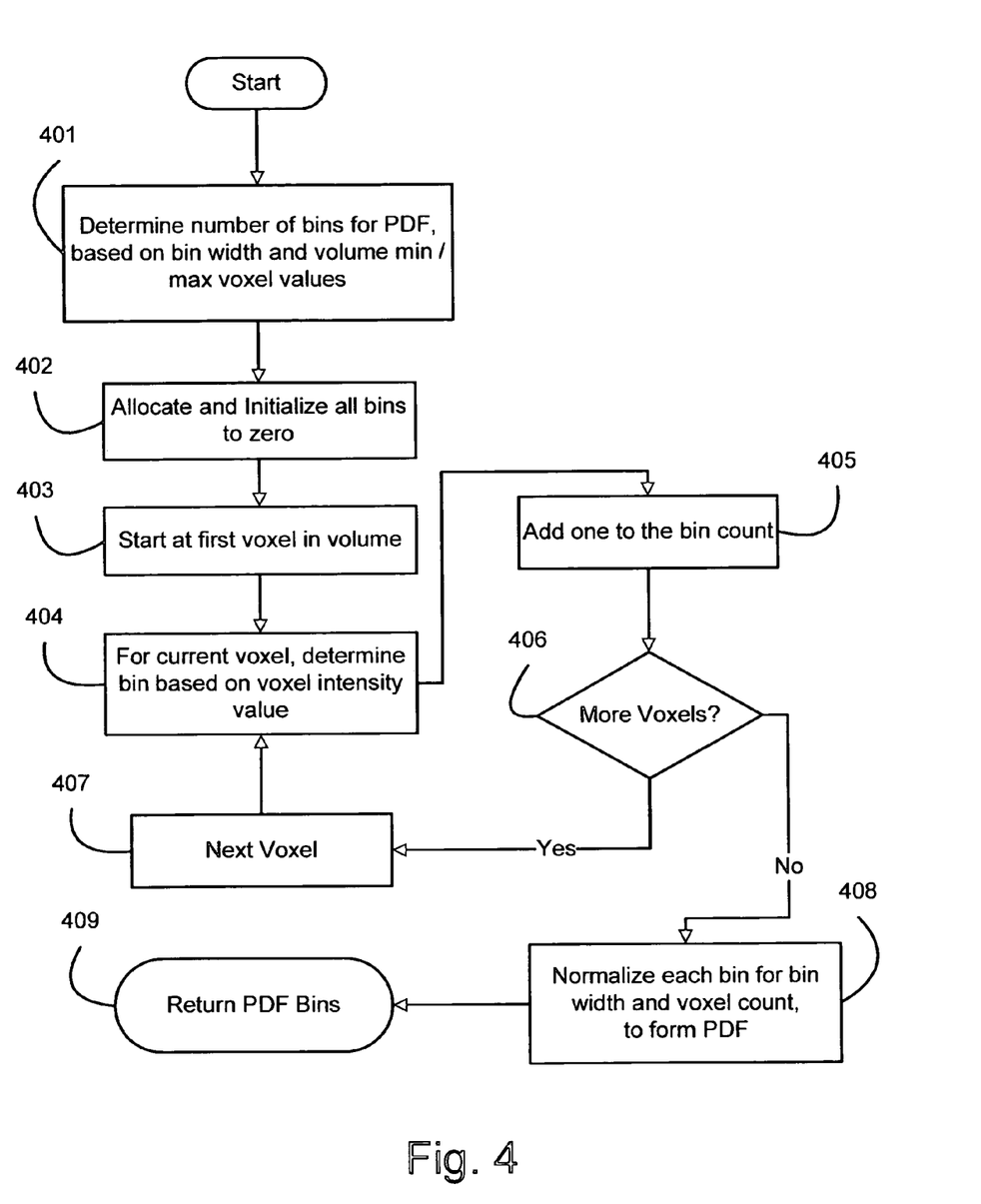
FIG. 4 is a flowchart depicting the evaluation of a basic PDF (normalized histogram).

The computation of a histogram for an image or volume can be represented as a simple algorithm that iterates over the image or volume points, accumulating pixel/voxel counts for each bin of the histogram. This is depicted in FIG. 4, for the related case of PDF computation. For purposes of treating the histogram (or PDF) analytically, the algorithmic form is not ideal.

For analysis, a functional description of the histogram is more appropriate. The functional description relates the value of each histogram bin to some function of pixel/voxel values, summed over the image or volume. For a discrete image $I(x,y)$, the functional form of a simple histogram of the image is the set of bin values $H_i$ given by $$H_i = \sum_y \sum_x u[I(x, y) - mid_i] \quad (1)$$

where $mid_i$ is the midpoint of bin i, and $u(r)$ is the histogram's binning kernel, defined by the scaled discrete unit impulse with width w $$u(r) = \begin{cases} 1 & \text{if } -\frac{w}{2} \leq r < \frac{w}{2} \\ 0 & \text{otherwise} \end{cases} \quad (2)$$

In the case of a continuous image, the image is described as a scalar field $I(\vec{r})$ and the histogram function becomes an integral over this field $$H_i = \int\int_I u[I(\vec{r}) - mid_i]d\vec{r} \quad (3)$$

The probability density function (PDF) of the image can be obtained by converting the histogram to a continuous function and normalizing by the image area A $$p(v) = \frac{1}{A}\int\int_I \delta[I(\vec{r}) - v]d\vec{r} \quad (4)$$

where $\delta(r)$ is the Dirac mass defined as the generalized function $$\delta(r) = 0 \quad (5)$$

for $r \neq 0$ $$\int_{-\infty}^{\infty} \delta(r)dr = 1$$

The PDF is more conducive to the following derivation, so it will be the focus.

Theory of Operation-Partial Derivatives of the PDF with Respect to Changes in the Underlying Image or Volume In the case of the inverse planning problem, generally the dose grid volume is a function of some parameters (typically beamlet weights). Then the problem is one of finding the optimal set of parameters that minimize (maximize) an objective function, which is itself a function of the image's histogram or PDF.

If the number of parameters is large, the solution can significantly benefit from gradient-based optimizations. In order to apply an effective gradient optimization, we need to analytically derive the partial derivatives of the PDF with respect to the parameters of the process. So we want to be able to compute $$\frac{\partial p(v)}{\partial \rho_j} = \frac{\partial}{\partial \rho_j}\left[\frac{1}{A}\int\int_I \delta[I(\vec{r}) - v]d\vec{r}\right] \quad (6)$$

$$= \frac{1}{A}\int\int_I \frac{\partial}{\partial \rho_j}\delta[I(\vec{r}) - v]d\vec{r}$$

for the set of parameters $\rho_j$ controlling the process that is modifying the image or volume.

We immediately run into difficulty because, as was observed for Hristov's formulation, the derivative of the Dirac mass is either zero or undefined. To address this problem, note that essentially the Dirac mass is here used as the PDF for a single point on the image. That is, if we assume that each pixel's value is known with absolute certainty, then the PDF of the image at that point is a Dirac mass centered on the pixel value. The offset by v is a way of shifting the mass into the proper "bin" of the image point PDF. So the image point PDF at point $\vec{r}$ is given by $$p_{\vec{r}}(v) = \delta[I(\vec{r}) - v] \tag{7}$$

which is the integrand from equation (4).

However, for real images, the value of a single pixel is not known with absolute certainty, so the pixels are better described by other distributions. Specifically, we can assume that a pixel value is a gaussian-distributed random variable with some known (constant) sigma value. In this case the PDF for the image at point $\vec{r}$ is given by $$p_{\vec{r}}(v) = \frac{1}{\sqrt{2\pi\sigma^2}} \exp\left[-\frac{[I(\vec{r}) - v]^2}{2\sigma^2}\right] \tag{8}$$
$$= g_\sigma[I(\vec{r}) - v]$$

Then the total image PDF is computed as $$p(v) = \frac{1}{A} \int\int_I p_{\vec{r}}(v) d\vec{r} \tag{9}$$

The σ parameter for an acquired image would typically be obtained by modeling the physical image formation process; for instance, by measuring the modulation transfer function of the image equipment. In our case, because we are incorporating a process that is modifying the image, we will attempt to derive a by propagating uncertainty in the process parameters. This technique is described in more detail below.

Using a gaussian as the image point PDF resolves the problem with the derivative of the Dirac mass, because the gaussian has a more amenable derivative. Now the partial derivative of the total image PDF can be expressed as $$\frac{\partial p(v)}{\partial \rho_j} = \frac{1}{A} \int\int_I \frac{\partial p_{\vec{r}}(v)}{\partial \rho_j} d\vec{r} \tag{10}$$

The derivative of each image point PDF [equation (8)] is given by $$\frac{\partial p_{\vec{r}}(v)}{\partial \rho_j} = \frac{1}{\sqrt{2\pi\sigma^2}} \exp\left[-\frac{[I(\vec{r}) - v]^2}{2\sigma^2}\right]\left[-\frac{I(\vec{r}) - v}{\sigma^2}\right]\frac{\partial I(\vec{r})}{\partial \rho_j} \tag{11}$$
$$= g'_\sigma[I(\vec{r}) - v]\frac{\partial I(\vec{r})}{\partial \rho_j}$$

where $g'_\sigma$ is the derivative-of-gaussian (DOG) function.

Substituting equation (11) into equation (10) results in an analytical expression for the partial derivative of the PDF with respect to a parameter modifying the underlying image.

Theory of Operation-Partial Derivative of a DVH with Respect to Beamlet Weights

In the present invention, the "image" being synthesized is the total dose volume resulting from the current set of weighted beamlets. The PDF is then the relative differential DVH, similar to Lian's approach. The set of parameters $\rho_j$ are the beamlet weights for all beams. So we need to derive the form of equation (10) for this specific case.

We are given a set of beamlet doses, which are volumetric scalar fields describing the normalized radiation deposited for each beamlet. Each beamlet also has an associated weight. The total dose deposited is the sum of each beamlet dose multiplied by the corresponding beamlet weight.

$$D_{total}(\vec{r}) = \sum_N w_n D_n(\vec{r}) \tag{12}$$

where $D_n(\vec{r})$ is the dose contributed by beamlet n at point $\vec{r}$ and $w_n$ is the weight of beamlet n.

The PDF, or relative differential DVH, is formed within a specified VOI based on the total dose. The DVH curve is given by $$DVH(v) = \frac{1}{A_{VOI}} \int\int_{VOI} p_{\vec{r}}(v) d\vec{r} \tag{13}$$

where $A_{VOI}$ is the area of the VOI for the DVH and $$p_{\vec{r}}(v) = g_\sigma[D_{total}(\vec{r}) - v] \tag{14}$$

The partial derivatives of the DVH with respect to the beamlet weights are then $$\frac{\partial}{\partial \vec{w}} DVH(v) = \frac{1}{A_{VOI}} \int\int_{VOI} \frac{\partial p_{\vec{r}}}{\partial \vec{w}} d\vec{r} \tag{15}$$

where $\vec{w}$ is the beamlet weight vector and $$\frac{\partial p_{\vec{r}}(v)}{\partial w_n} = g'_\sigma[D_{total}(\vec{r}) - v]\frac{\partial D_{total}(\vec{r})}{\partial w_n} \tag{16}$$
$$= g'_\sigma[D_{total}(\vec{r}) - v]D_n(\vec{r})$$

Substituting equation (16) into equation (15) results in the analytical expression of the partial derivative of the relative differential DVH with respect to changes in beamlet weight. This is the expression that needs to be efficiently evaluated by a gradient-based inverse planning algorithm.

Theory of Operation-Sigma Estimation and Multiresolution Optimization

The estimation of the gaussian sigma is crucial to an effective optimization. Initially, we generate estimates for the initial beamlet weight parameters based on the mean beamlet weights over some chosen sample of treatment plans. This sample of treatment plans can also used to generate a covariance matrix for the beamlet weights. Based on the covariance matrix, we can propagate the uncertainty in the beamlet weights to uncertainty in the dose value at a particular point. By averaging this uncertainty across all points in the dose matrix, we derive the sigma for the invariant gaussian distribution.

As the optimization proceeds, the sigma estimation will become smaller due to increased certainty in the image point PDFs. The optimization process itself can be viewed as a type of estimation process, in which case we can compute the estimation residual using a suitably chosen discrete causal filter applied to the last n state vectors examined by the optimization. This residual, in the form of a state vector covariance matrix, describes the uncertainty in the current estimate of the optimal state vector.

This state vector covariance matrix can be propagated to the dose matrix, resulting in an uncertainty in dose value at a particular point. Averaging this uncertainty across all points in the dose matrix results in an updated sigma parameter. This sigma parameter is used to compute the objective function for the next iteration.

This iterative update of the sigma can be conveniently coupled to a multiresolution representation of the dose matrix, so that early in the optimization the DVH is evaluated over a lower resolution dose matrix, and as optimization proceeds the resolution increases. The coupling is accomplished by propagating the dose point uncertainty to positional uncertainty (spatial resolution) using the gradient of the dose matrix. The average over all dose points is used to determine the resolution for DVH calculation at the current iteration.

Theory of Operation-Histogram-Matching Objective Functions

In order to use the histogram or PDF partial derivatives in optimization, a scalar valued objective function is needed. The simplest of these is a least-squares match of the histogram or PDF with a target histogram or PDF. For a PDF, this is an integral over the domain of the PDF, which are the possible pixel intensity values.

$$E = \int_{\min v}^{\max v} [p_{target}(v) - p(v)]^2 dv \tag{17}$$

where $P_{target}(v)$ is the specified target PDF. The gradient of the histogram-matching objective function with respect to a parameter vector $\vec{\rho}$ is $$\nabla_{\vec{\rho}} E = \int_{\min v}^{\max v} 2[p_{target}(v) - p(v)] \frac{\partial p(v)}{\partial \vec{\rho}} dv \tag{18}$$

For beamlet weight optimization, the expression for $$\frac{\partial p(v)}{\partial \vec{\rho}}$$

is given by equation (16).

Least-squares matching is suitable for matching general curves and some other functions. However, because a PDF represents probabilities, there are other metrics that may perform better. One of these is the Kullback-Liebler divergence, or relative entropy. This is a measure of the similarity between probability distributions, for which it is a better suited similarity measure because it reduces the importance of matching for parts of the distribution with low frequencies.

The Kullback-Liebler divergence between two PDFs p(v) and q(v) is defined as $$\mathcal{KL}(q, p) = \int_{\min v}^{\max v} q(v) \log \frac{q(v)}{p(v)} dv \tag{19}$$

To create an objective function for histogram matching, we use the Kullback-Liebler divergence between the target PDF and the current PDF $$E = \int_{\min v}^{\max v} p_{target}(v) \ln \frac{p_{target}}{p(v)} dv \tag{20}$$

$$= \int_{\min v}^{\max v} p_{target}(v) [\ln p_{target}(v) - \ln p(v)] dv$$

Taking the gradient of the objective function, $$\nabla_{\vec{\rho}} E = -\int_{\min v}^{\max v} \frac{p_{target}(v)}{p(v)} \frac{\partial p(v)}{\partial \vec{\rho}} dv \tag{21}$$

where $$\frac{\partial p(v)}{\partial \vec{\rho}}$$

is again given by equation (16).

Description-Gradient-Based Optimization

Figure 2:
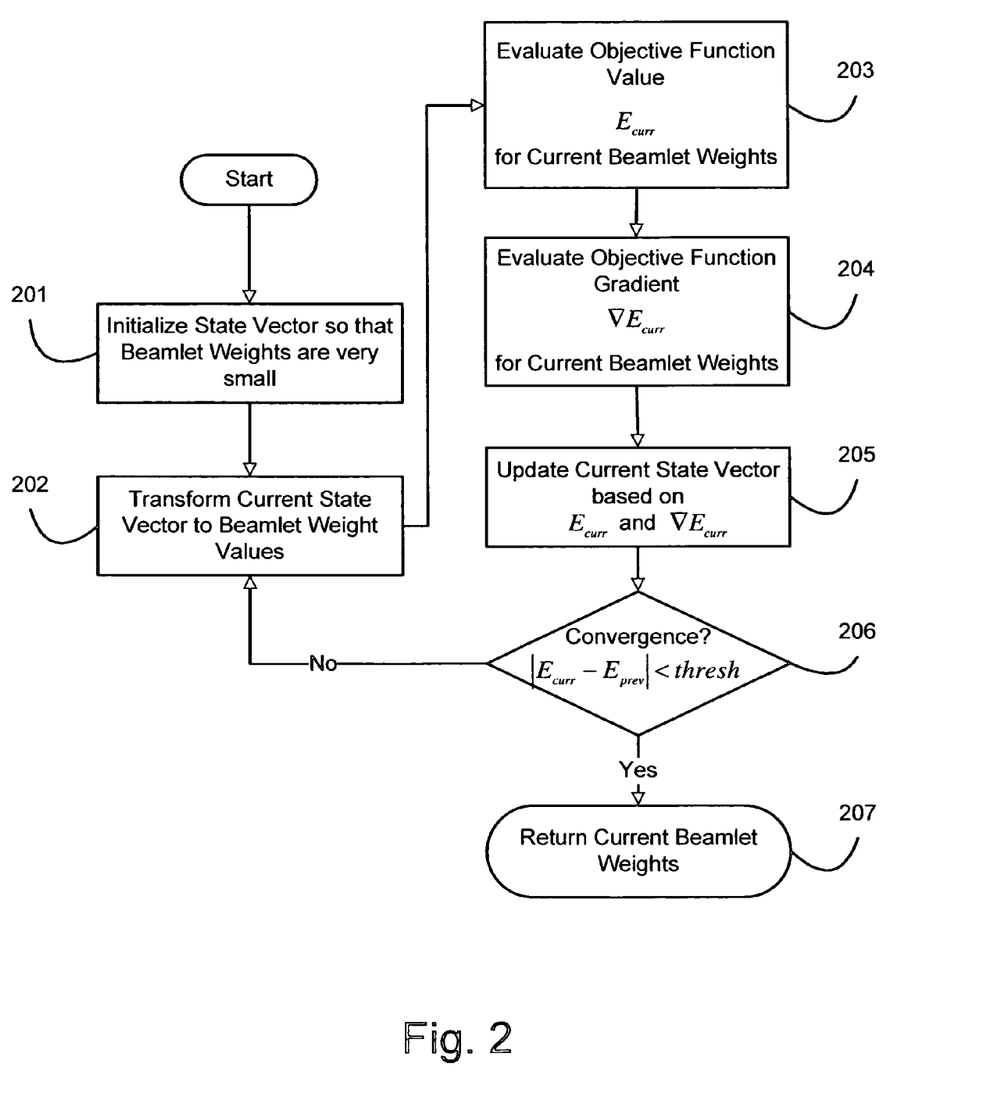
FIG. 2 is a flowchart depicting the conjugate-gradient optimization algorithm applied to a histogram-matching objective function.

There are a number of optimization algorithms available that can take advantage of gradient information for the objective function. The conjugate gradient optimization has favorable convergence properties, and is able to take advantage of our objective function's good directional conjugacy. The preferred implementation of the present invention uses a conjugate gradient algorithm to find the objective function optimum.

FIG. 2 is a flow chart for the conjugate gradient algorithm, as applied to the inverse planning problem using our objective function.

The initialization of the state vector occurs in 201. The state vector holds the current value of the parameters for the optimization. This current value is initialized to a state that corresponds to all beamlets having weights of nearly zero.

The beamlet weights are not set to zero, because the state vector elements are related to beamlet weight by a sigmoidal transformation that prevents negative values, which are physically impossible. This transformation also prevents the weight of any single beamlet from becoming too large (which is clinically unacceptable). In order to perform this transformation, 202 shows the transformation of state vector elements to corresponding beamlet weights.

Next the algorithm evaluates the objective function 203 and its gradient 204 for the current state vector value. This is described in detail below.

After evaluating the objective function value and its gradient, the conjugate gradient algorithm then 205 updates the current state vector value using the update rule for the conjugate gradient algorithm. Details of the state vector update for the conjugate gradient algorithm can be found in Press et. al. (1993).

To test if the optimization is complete, a convergence criterion is defined for the conjugate gradient algorithm, based on a user-specified tolerance for the objective function. If the successive values of the objective function are within the tolerance of each other, then in 206 the optimization has converged, and it terminates and returns the current state vector value 207. Details of the convergence condition for the conjugate gradient algorithm can also by found in Press et. al. (1993).

If the convergence criterion has not been met, then the algorithm continues in to another iteration.

Description-Histogram Matching Objective Function

Figure 3:
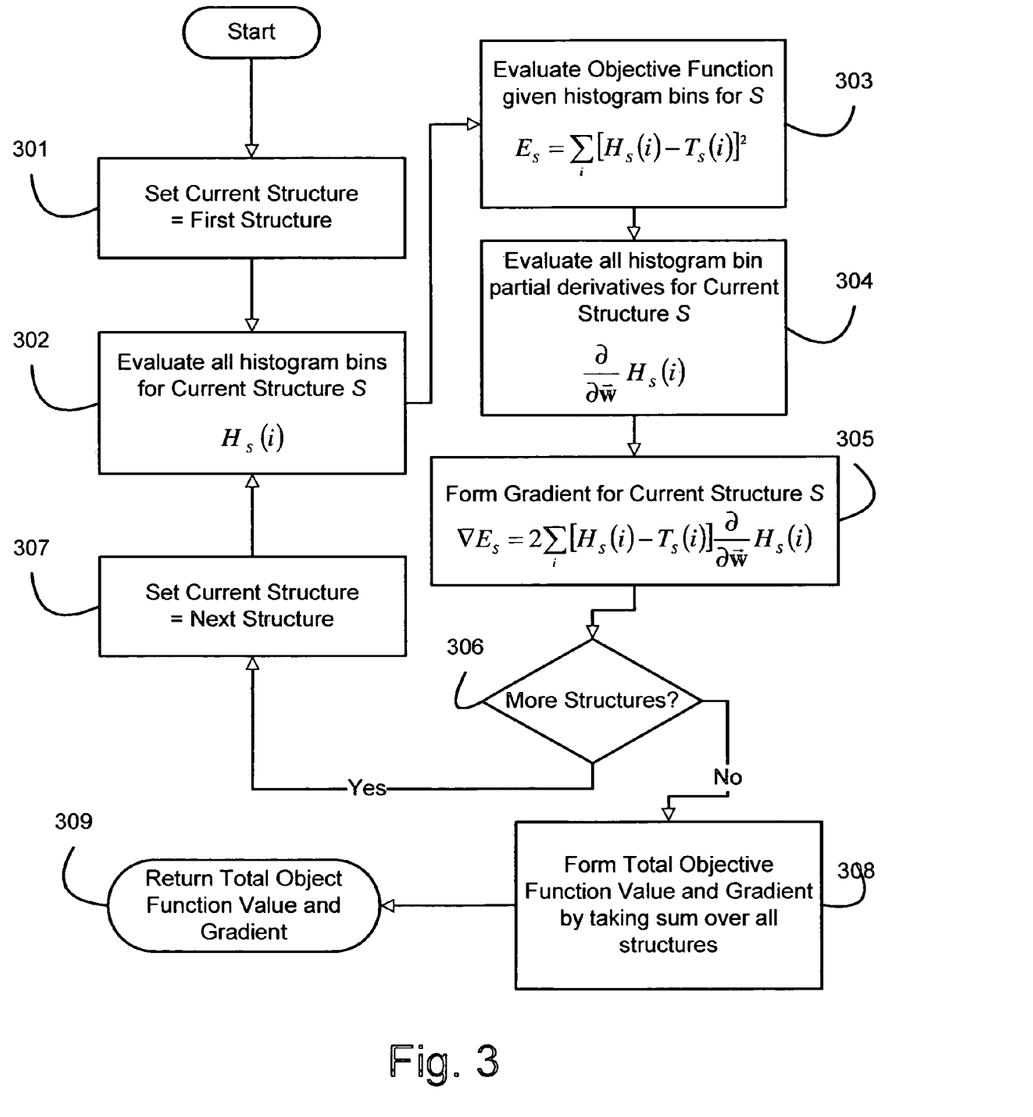
FIG. 3 is a flowchart depicting the evaluation of the histogram-matching objective function value and gradient.

The objective function evaluation for a histogram matching objective function is described in the flowchart of FIG. 3.

The outer loop of the objective function evaluation is the iteration over all structures, or volumes-of-interest (VOIs), for which target DVH curves have been defined for inverse planning. The first step 301 is to initialize the current structure to the first structure.

Then 302 all histogram bins are evaluated for the current structure. This is described below.

Given the histogram bins, the value of the objective function is then evaluated 303. Note that this is only the term of the objective function for the current structure. This is depicted in the formulation for least-squares matching as given in equation (17); for Kullback-Liebler divergence, use the formula in equation (20).

Then 304 the partial derivatives of the histogram bins are computed. This is described below.

With the partial derivatives of the histogram bins, the gradient of the objective function can be evaluated 305. Note that this is only the gradient of the objective function for the current structure. This is the least-squares formulation given in equation (18); for Kullback-Liebler divergence, use the formula in equation (21).

Now, if more structures remain, iterate 306 and continue for the next structure 307.

If no more structures remain, form the total objective function value and gradient 308 by summing the results from all structures. Finally, return these values to the caller 309.

Description-Evaluating the Gaussian PDF

Now a computationally efficient form for the gaussian total image PDF, equation (9), is derived. Almost all images are represented as an array of discretely sampled voxels with finite precision. The most computationally efficient approximation for the original continuous unit impulse PDF in equation (4) is to first compute the histogram and then to normalize the bin counts for the image size and bin width, as depicted in FIG. 4.

The first initialization step is to determine the number of bins 401, based on bin width and min/max values for the voxels.

Next, all bins must be allocated and initialized to zero 402 prior to beginning the actual calculation.

Then, beginning with the first voxel 403, the bin to which the current voxel belongs is determined 404. This bin value count is incremented 405. Iteration occurs if there are more voxels 406, and the bin update repeats for the next voxel 407.

If there are no more voxels to process, the bin values are processed. This includes normalizing for bin width and for the total number of voxels 408.

Finally, the resulting bins are returned to the calling function 409.

In the case of the PDF, adding 1 to each bin corresponds to the fact that the integral of the continuous unit impulse is one over an infinitesimally small range. Since each continuous unit impulse can only belong to one bin, we only need to determine which bin it belongs to and then add 1 to that bin's count.

When we switch to using the gaussian image point PDF in equation (8), each voxel may now potentially contribute to multiple bins because the image point PDF is distributed over multiple bins. This could seriously impede the performance of the algorithm.

A more efficient approach for computing equation (9) can be used if the image point PDFs are spatially invariant (that is, if they are all shifted versions of the same distribution). This is the case for the assumed gaussian image point PDF. Then the procedure depicted in FIG. 5 can be used. This procedure can significantly increase the efficiency of the algorithm by deferring the "spread" of each voxel's contribution to the PDF until the last step.

Figure 5:
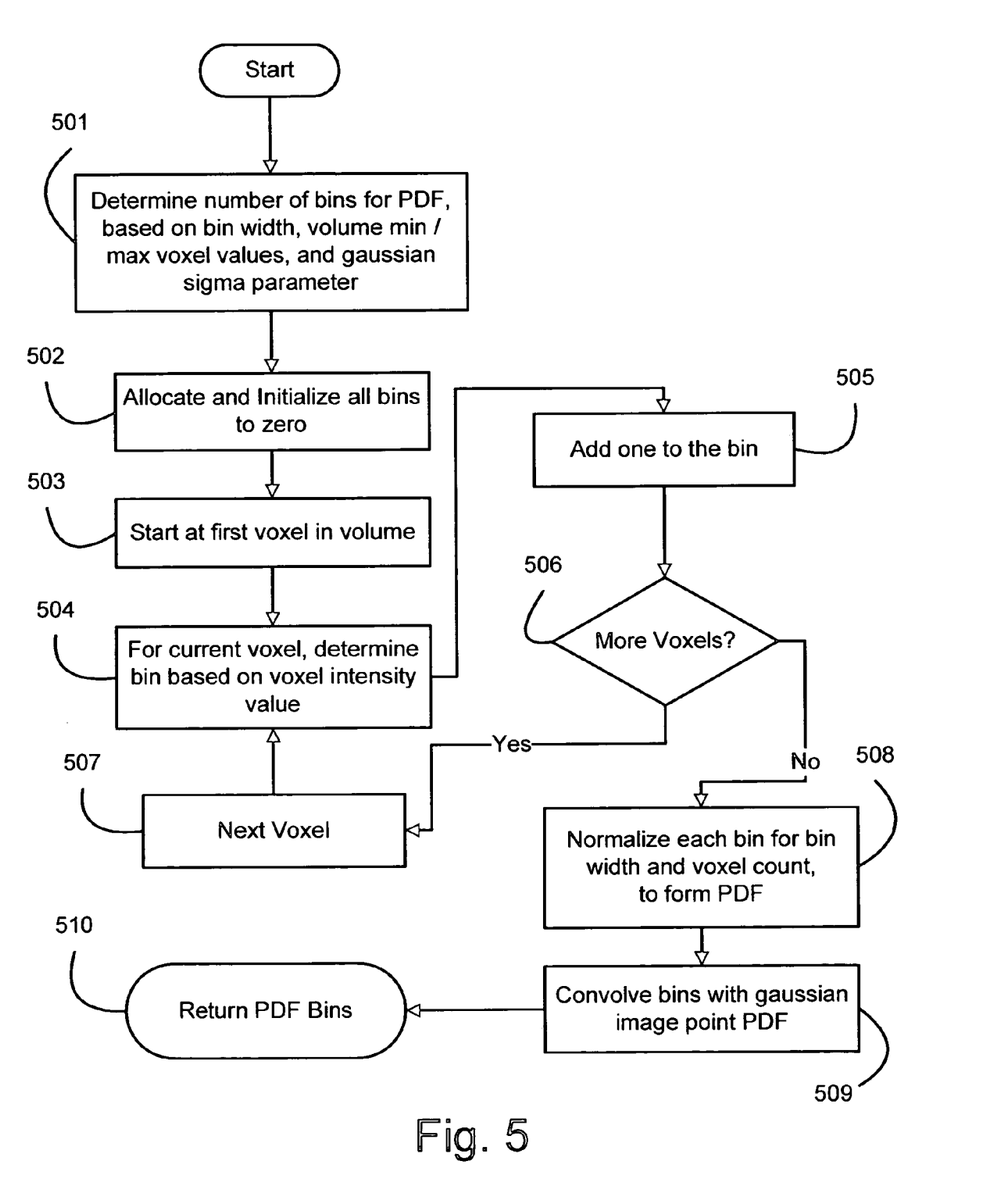
FIG. 5 is a flowchart depicting a method of efficiently evaluating the gaussian PDF.

The first initialization step is to determine the number of bins 501, based on the gaussian sigma parameter and min/max values for the voxels.

Next, all bins must be initialized to zero 502 prior to beginning the actual calculation.

Then, beginning with the first voxel 503, the bin to which the current voxel belongs is determined 504. This bin value count is incremented 505. Iteration occurs if there are more voxels 506, and the bin update repeats for the next voxel 507.

If there are no more voxels to process, the bin values are processed. This includes normalizing for bin width and for the total number of voxels 508.

The final step is to "spread" the voxels contribution. This is done by convolving the bins by the binning kernel 509. By deferring this step to the end, after all bins are accumulated, significant performance increases can be realized.

Finally, the resulting bins are returned to the calling function 510.

Description-Evaluating the Gradient of the Gaussian PDF

In order to compute the partial derivate of the PDF described in equation (15), we need to look carefully at the form of the partial derivative in equation (16). It is essentially a derivative-of-gaussian (DOG) scaled by the value of the image's partial derivative at that point. The DOG can be efficiently incorporated in the same way as the gaussian image point PDF, by post-convolving after forming the original PDF.

Figure 6:
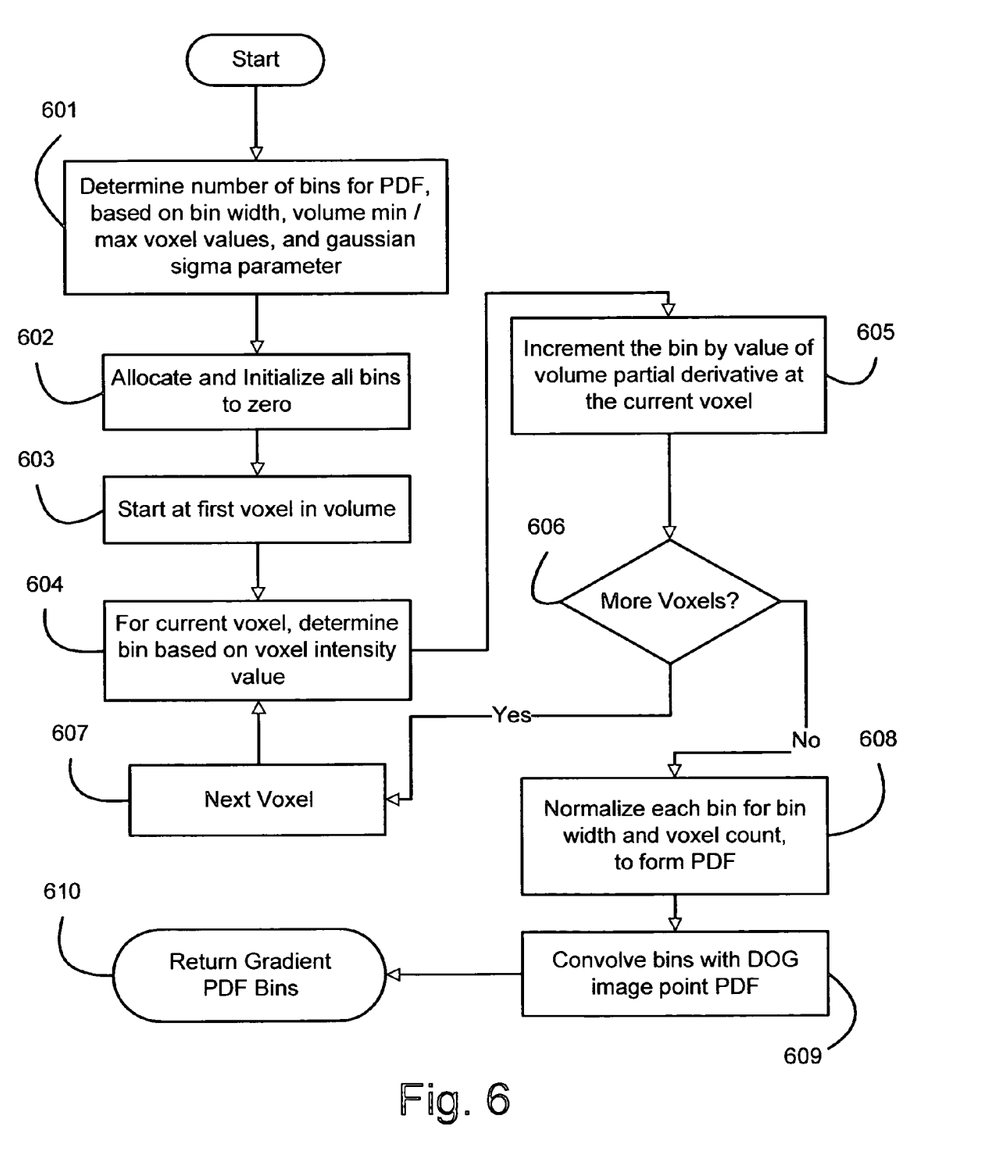
FIG. 6 is a flowchart depicting a method of efficiently calculating one component of the gradient of the gaussian PDF.

Incorporating the image partial derivative involves scaling each voxel's contribution to its central bin proportionally by the value of the image partial derivative. The resulting procedure for computing equation (15) is depicted in FIG. 6.

The initialization step is to determine the number of bins 601, based on the gaussian sigma parameter and min max values for the voxels.

Next, all bins must be allocated initialized to zero 602 prior to beginning the actual calculation.

Then, beginning with the first voxel 603, the bin to which the current voxel belongs is determined 604. The bin value is incremented by an amount equal to the value of the corresponding volume partial derivative, at that point on the image 605. Iteration occurs if there are more voxels 606, and the bin update repeats for the next voxel 607.

If there are no more voxels to process, the bin values are processed. This includes normalizing for bin width and normalizing for the total number of voxels 608.

Finally, the resulting bins are convolved with the DOG kernel 609, to form the final partial derivative.

The resulting bins are returned to the calling function 610.

Note that this procedure is described for only one of the partial derivatives of interest. It needs to be repeated for each partial derivative in order to form the complete gradient. In this case, the volume partial derivatives in 605 are all of the beamlet dose volumes, with each beamlet corresponds to one element of the gradient.

Operation of the Preferred Embodiment

In the preferred embodiment, the algorithm is implemented within application software running on a general-purpose desktop computer or workstation. The workstation is connected via network to a CT scanner, from which it retrieves planning CT scans. The workstation is also connected via network to a clinical radiation delivery system, to which it sends the final planning parameters.

The user begins by retrieving a planning CT scan for a patient and opening the CT scan in the application. The application provides a variety of tools for manually and automatically delineating volumes-of-interest (VOIs). These may include tools for manually outlining VOIs on each CT image slice, tools for automatically segmenting the CT volume, and tools for manipulating existing VOIs.

After all relevant VOIs are defined, the user selects the number and orientation of the radiation beams. Also the user must specify the position of the beams' isocenter, which is the common point at the intersection of all central rays. With this information, the application can calculate the dose contribution for each beamlet within the specified beams.

With the beamlet dose calculated, the user must now specify prescription information for all relevant structures/VOIs in the form of target DVH curves. This can be done interactively on the DVH graph, or using a dialog-based mechanism for common curve shapes. Additional parameters for the inverse planning algorithm, such as importance weights for each structure, can also be specified.

With the needed parameters specified, the application can now compute an optimal plan and display the resulting dose distribution to the user. The dose is displayed both in 3D views, superimposed with structure outlines on the CT images, and in the form of the DVH graph. If the user is not satisfied with the resulting dose, they may alter the prescription or other parameters and re-optimize. Alternatively, they may make adjustments to the defined structures and re-optimize.

If the application is running on sufficiently powerful hardware, it is possible to dynamically re-optimize the plan as the parameter or structure changes are being made. This creates a very compelling and intuitive interface, as the user is now able to dynamically adjust parameters and immediately see the result. This allows the user to quickly understand the effect of parameter changes on the resulting plan, and to obtain better quality plans in a shorter amount of time.

Once the user is satisfied with the resulting plan, the plan information is transmitted via network to the treatment delivery system so that it can be delivered to the patient.

Conclusion, Ramification, and Scope

A method is described for fast inverse planning of IMRT treatment plans. The method relies on a computationally efficient algorithm for evaluating the gradient of a general class of objective functions, and also on the efficient optimization that is realized due to the high directional conjugacy of the objective functions. Several types of clinically relevant objective functions that belong to this class are described. The computational evaluation relies on operations that are commonly used for signal- and image-processing, and so can benefit from a number of well-known acceleration techniques.

The resulting algorithm is sufficiently fast that the user is able to quickly and intuitively derive a clinically advantageous plan, by interactively modifying the optimization inputs and observing the resulting optimized plan.

Although the description above contains much specificity, these should not be construed as limiting the scope of the invention but merely providing illustrations of some of the presently preferred embodiments of this invention. Thus the scope of the invention should be determined by the appended claims and their legal equivalents, rather than by the examples given.

What is claimed is:

1. A method of planning and delivering a clinical radiation treatment, comprising the steps of:
    (a) defining 3-dimensional volumes-of-interest (VOIs) corresponding to clinically salient targets or organs-at-risk within the patient,
    (b) specifying for each 3-dimensional VOI a clinically advantageous radiation dose distribution,
    (c) generating an initial set of estimated treatment parameter values and associated treatment parameter probability density functions (PDFs),
    (d) calculating for each VOI an estimated radiation dose distribution from said treatment parameter PDFs, said estimated radiation dose distribution defined in terms of said treatment parameter PDFs and calculated by mathematical integration over the function range of said treatment parameter PDFs,
    (e) calculating for each VOI a similarity measure between said estimated radiation dose distribution and said clinically advantageous radiation dose distribution,
    (f) calculating the mathematical gradient of said similarity measure with respect to said treatment parameter values by mathematical integration over the function range of said treatment parameter PDFs,
    (g) updating said treatment parameter values and said treatment parameter PDFs using said gradient such that said similarity measure is improved,
    (h) performing an optimization by repeating steps (d) through (g) until said treatment parameter values have reached a defined criteria for acceptability;
    (i) delivering treatment using the final treatment parameter values and a suitable clinical radiation generation device;
   whereby said final treatment parameter values produce a radiation dose distribution substantially similar to said clinically advantageous radiation dose distribution.

2. The method of (1), wherein said treatment parameter values are individual beamlet weights for the plurality of beamlets comprising the radiation treatment; whereby an optimized treatment plan is generated that is deliverable by an intensity-modulated radiation treatment (IMRT) delivery system.

3. The method of (1), wherein
    (a) said clinically advantageous radiation dose distribution is specified as a probability density function (PDF) of radiation dose per VOI,
    (b) said similarity measure is an information theoretic PDF similarity measure between said estimated radiation dose distribution and said clinically advantageous radiation dose distribution.

4. The method of (3), wherein said PDF similarity measure is the Kullback-Liebler divergence.

5. The method of (3), wherein said PDF similarity measure is the squared difference of PDFs.

6. A method of planning and delivering a clinical radiation treatment, comprising the steps of:
(a) defining 3-dimensional volumes-of-interest (VOIs) corresponding to clinically salient targets or organs-at-risk within the patient,
(b) specifying for each 3-dimensional VOI a clinically advantageous radiation dose distribution in the form of a probability density function (PDF) of radiation dose,
(c) generating an initial set of estimated treatment parameter values,
(d) determining for each VOI an estimated radiation dose distribution based on said treatment parameter values in the form of a PDF of radiation dose,
(e) calculating for each VOI an information theoretic PDF similarity measure between said estimated radiation dose distribution and said clinically advantageous radiation dose distribution,
(f) calculating the mathematical gradient of said PDF similarity measure with respect to said treatment parameter values,
(g) updating said treatment parameter values using said gradient such that said PDF similarity measure is improved,
(h) performing an optimization by repeating steps (d) through (g) until said treatment parameter values have reached a defined criteria for acceptability;
(i) delivering treatment using the final treatment parameter values and a suitable clinical radiation generation device;
whereby said PDF similarity measure is substantially more proportional to the clinical advantageousness of the treatment parameters.

7. The method of (6), wherein said treatment parameter values are individual beamlet weights for the plurality of beamlets comprising the radiation treatment;
whereby an optimized treatment plan is generated that is deliverable by an intensity-modulated radiation treatment (IMRT) delivery system.

8. The method of (6), wherein
(a) an initial set of treatment parameter probability density functions (PDFs) associated with said treatment parameter values is generated,
(b) said estimated radiation dose distribution is defined in terms of said treatment parameter PDFs, and calculated by mathematical integration over the function range of said treatment parameter PDFs,
(c) said gradient is calculated by mathematical integration over the function range of said treatment parameter PDFs,
(d) said treatment parameter PDFs are updated using said gradient at each iteration of the optimization.

9. The method of (6), wherein said PDF similarity measure is the Kullback-Liebler divergence.

10. The method of (6), wherein said PDF similarity measure is the squared difference of PDFs.

11. An apparatus for planning and delivering a clinical radiation treatment, comprising:
(a) means for defining 3-dimensional volumes-of-interest (VOIs) corresponding to clinically salient targets or organs-at-risk within the patient,
(b) means for specifying for each 3-dimensional VOI a clinically advantageous radiation dose distribution,
(c) means for generating an initial set of estimated treatment parameter values and associated treatment parameter probability density functions (PDFs),
(d) means for calculating for each VOI an estimated radiation dose distribution from said treatment parameter PDFs, said estimated radiation dose distribution defined in terms of said treatment parameter PDFs and calculated by mathematical integration over the function range of said treatment parameter PDFs,
(e) means for calculating for each VOI a similarity measure between said estimated radiation dose distribution and said clinically advantageous radiation dose distribution,
(f) means for calculating the mathematical gradient of said similarity measure with respect to said treatment parameter values by mathematical integration over the function range of said treatment parameter PDFs,
(g) means for updating said treatment parameter values and said treatment parameter PDFs using said gradient such that said similarity measure is improved,
(h) means for performing an optimization by repeating steps (d) through (g) until said treatment parameter values have reached a defined criteria for acceptability;
(i) means for delivering treatment using final treatment parameter values and a suitable clinical radiation generation device;
whereby said final treatment parameter values produce a radiation dose distribution substantially similar to said clinically advantageous radiation dose distribution.

12. The apparatus of (11), wherein said treatment parameter values are individual beamlet weights for the plurality of beamlets comprising the radiation treatment;
whereby an optimized treatment plan is generated that is deliverable by an intensity-modulated radiation treatment (IMRT) delivery system.

13. The apparatus of (11), wherein
(a) said clinically advantageous radiation dose distribution is specified as a probability density function (PDF) of radiation dose per VOI.
(b) said similarity measure is an information theoretic PDF similarity measure between said estimated radiation dose distribution and said clinically advantageous radiation dose distribution.

14. The apparatus of (13), wherein said PDF similarity measure is the Kullback-Liebler divergence.

15. The apparatus of (13), wherein said PDF similarity measure is the squared difference of PDFs.

* * * * *